(12) United States Patent
Notter

(10) Patent No.: US 9,415,185 B2
(45) Date of Patent: Aug. 16, 2016

(54) INTRAVENOUS INDWELLING CATHETER

(75) Inventor: Michael Notter, Berlin (DE)

(73) Assignee: Michael Notter (DE)

( * ) Notice: Subject to any disclaimer, the term of this patent is extended or adjusted under 35 U.S.C. 154(b) by 2319 days.

(21) Appl. No.: 11/719,720

(22) PCT Filed: Oct. 26, 2005

(86) PCT No.: PCT/DE2005/001945
§ 371 (c)(1),
(2), (4) Date: Mar. 10, 2009

(87) PCT Pub. No.: WO2006/053516
PCT Pub. Date: May 26, 2006

(65) Prior Publication Data
US 2010/0137744 A1    Jun. 3, 2010

(30) Foreign Application Priority Data
Nov. 19, 2004    (DE) .......................... 10 2004 055 989

(51) Int. Cl.
| A61B 5/00 | (2006.01) |
| A61M 25/00 | (2006.01) |
| A61B 5/15 | (2006.01) |
| A61B 5/153 | (2006.01) |
| A61M 39/02 | (2006.01) |

(52) U.S. Cl.
CPC .......... *A61M 25/0014* (2013.01); *A61B 5/1405* (2013.01); *A61B 5/15003* (2013.01); *A61B 5/153* (2013.01); *A61B 5/15074* (2013.01); *A61B 5/150389* (2013.01); *A61B 5/150503* (2013.01); *A61B 5/150755* (2013.01); *A61M 2039/0202* (2013.01)

(58) Field of Classification Search
CPC .............. A61B 5/1405; A61B 5/1422; A61M 25/0014
USPC ......................................... 600/581, 576, 582
See application file for complete search history.

(56) References Cited

U.S. PATENT DOCUMENTS

| 3,405,706 | A |   | 10/1968 | Cinqualbre ........................ 128/2 |
| 4,079,738 | A | * | 3/1978 | Dunn et al. ............... 604/164.05 |
| 4,444,203 | A | * | 4/1984 | Engelman ..................... 600/576 |
| 4,653,511 | A | * | 3/1987 | Goch et al. .................... 600/576 |
| 5,270,003 | A |   | 12/1993 | Bernes et al. .................... 422/44 |
| 5,474,546 | A |   | 12/1995 | Ambrisco et al. ............ 604/411 |
| 6,296,624 | B1 |   | 10/2001 | Gerber et al. ............ 604/164.11 |
| 2002/0156431 | A1 |   | 10/2002 | Feith et al. .................... 604/247 |

FOREIGN PATENT DOCUMENTS

EP          0 910 988          1/2002

OTHER PUBLICATIONS

International Search Report PCT/DE2005/001945 dated Apr. 3, 2006.

\* cited by examiner

*Primary Examiner* — Lee S Cohen
*Assistant Examiner* — Emily Lloyd
(74) *Attorney, Agent, or Firm* — Ostrolenk Faber LLP

(57) ABSTRACT

The invention relates to an indwelling catheter in particular an intravenous indwelling catheter for emergency treatment. The catheter comprises a housing and a puncturing cannula, which can be introduced into and removed from the housing interior in the longitudinal direction of the housing and which extends through a front housing opening, in such a way that when the cannula is fully introduced, an entry opening is located outside the housing. A collection component stores a blood sample, the component being held in a displaceable manner on the housing with the aid of a fixing element and being displaced between a coupled position, in which a self-filling reservoir, which is configured in the collection component, is in contact with an exit opening of the cannula in order to receive a sample of blood that traverses the cannula and an uncoupled position, in which the reservoir is separated from the exit opening of the cannula and the collection component is held on the housing by the fixing element.

19 Claims, 1 Drawing Sheet

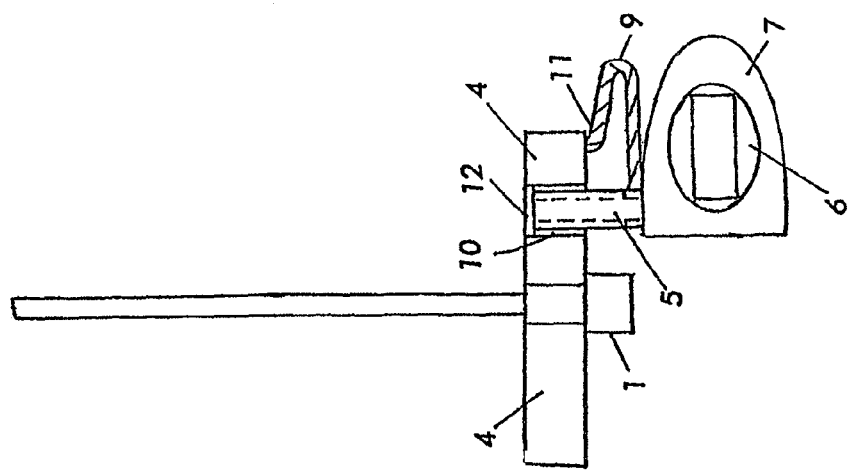
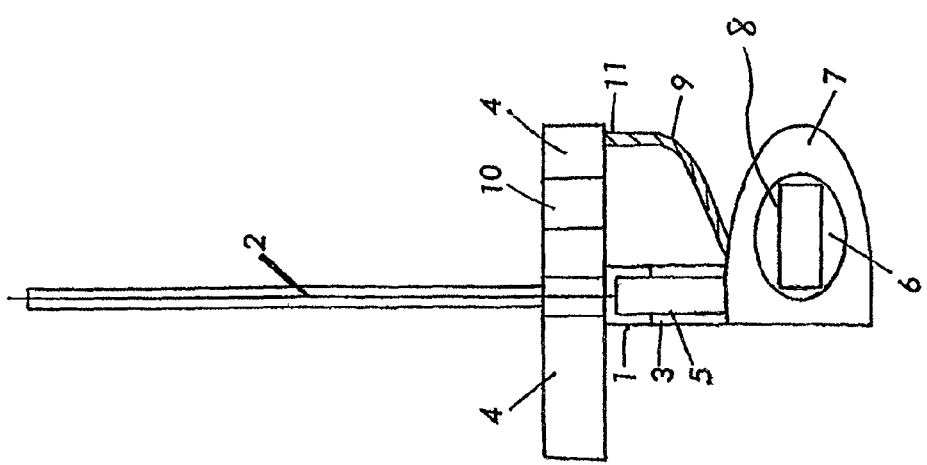

INTRAVENOUS INDWELLING CATHETER

CROSS REFERENCE TO RELATED APPLICATION

The present application is a 35 U.S.C. §§371 national phase conversion of PCT/DE2005/001945,filed Oct. 26, 2005, which claims priority of German Patent Application No.10 2004 055 989.9,filed Nov. 19, 2004, which are herein incorporated by reference. The PCT International Application was published in the German Language.

The invention relates to an indwelling catheter, in particular to an intravenous indwelling catheter for emergency/disaster treatment.

BACKGROUND OF THE INVENTION

Such indwelling catheters usually comprise a housing with a housing interior which runs in the longitudinal direction of the housing and extends between a front and a rear opening of the housing and is optionally connected to an injection valve formed in the region of the housing wall, via which injection valve drugs in liquid form can be administered to the patent following placement of the indwelling catheter. A cannula for puncturing the skin during the placement of the indwelling catheter is introduced into the housing interior. The cannula is introduced into the housing interior until an entry opening in the region of a tip of the cannula is arranged outside the housing and in front of the front opening. A rear end of the cannula is arranged in a grip piece, by means of which the cannula can be guided as it is introduced into the housing and as it is removed from the housing. The grip piece is usually inserted into a rear end of the housing when the cannula is introduced into the housing for placement of the indwelling catheter. A channel is formed in the grip piece and is connected to the exit opening at the rear end of the cannula.

Various closure or connection pieces, for example a Luer connection system, can be inserted into an end of the grip piece remote from the housing, in order to close the channel in the grip piece and/or connect it to other lines. During placement of the indwelling catheter, usually a closure piece is arranged in the rear end of the grip piece, wherein the interior of the closure piece is connected at one side to the channel in the grip piece and thus to the exit opening of the cannula and at the other side to an outflow opening. Arranged in the region of the outflow opening is an air-permeable filter, through which air can flow out when blood flows from the channel in the grip piece into the closure piece and thereby displaces the air. After placement of the indwelling catheter, usually the closure piece and the grip piece containing the cannula are removed, so that other connections can be connected to the housing in order to further treat the patient.

Indwelling catheters having a structure such as this are known in various embodiments. Usually, a support is also formed on the housing of the indwelling catheter, for example in the form of laterally protruding wings, in order to support the indwelling catheter on the skin of the patient.

Indwelling catheters are used both in the field of stationary patient treatment and in connection with treating patients in an emergency or disaster. When treating badly injured patients, there is often a need for emergency transfusions, particularly with erythrocyte concentrates, immediately after the patient has been admitted to the stationary treatment center. These may then lead to massive transfusions. In this case, it is necessary to be able to carry out the transfusion as quickly as possible using ABO-compatible stored supplies. This standard means that it is necessary to determine the emergency blood group (antigen determination on receiver erythrocytes). For this, just 0.1-0.5 ml of natural blood from the patient is required. Practice shows that emergency medical treatment by transfusion is made more difficult by the following circumstances:

Infusion with the plasma expander hydroxyethyl starch (HES), which is used to treat shock at the site of the accident, makes it more difficult to reliably determine the blood group or may even make this impossible within a short time since HES molecules can agglutinate with high-molecular-weight erythrocytes (pseudoagglutination).

Patients in severe hemorrhagic shock receive so-called "O Rh negative emergency blood supplies" immediately after being admitted to the rescue center. After the transfusion of emergency blood supplies, the patient's blood group can no longer be reliably determined (mixed field agglutination). Further treatment can then no longer take place with ABO-compatible blood supplies but rather must take place with supplies of blood group O. In particular, treatment of a number of patients at the same time or transfusion management in the event of a disaster or treatment of a number of patients at the same time is made more difficult as a result.

Ideally, the pretransfusion blood sample to determine the emergency blood group would be taken at the mobile site within the context of primary treatment. However, practice in rescue medicine shows that this does not happen since the priority is to ensure vital functions of the patient. The filling, clear identification and storing of test tubes of blood is a task that cannot be performed in practice during primary treatment in an emergency. For most patients, therefore, blood is not taken until the patient is delivered to the stationary treatment center.

Patients with severe hemorrhagic shock are the most likely to be affected by the risk of the blood group not being determined or not being clearly determined in the event of an emergency. These patients require plasma expanders in large quantity and emergency blood supplies with the greatest urgency.

SUMMARY OF THE INVENTION

The task of the invention is to provide an improved indwelling catheter, by means of which reliable collection of a blood sample is ensured, in particular even in the event of an emergency or disaster.

According to the invention, this task is solved by an indwelling catheter.

The invention encompasses the concept of an indwelling catheter, in particular an intravenous indwelling catheter for emergency treatment, comprising a housing and a puncturing cannula, which is removably introduced into a housing interior in the longitudinal direction of the housing and extends through a front housing opening in such a way that an entry opening of the cannula is arranged outside the housing at least in a fully introduced position of the cannula, wherein a collection component for storing a blood sample is provided, which collection component is held in a movable manner on the housing by means of a fixing element and can be displaced between a coupled position, in which a self-filling reservoir formed in the collection component is connected to an exit opening of the cannula in order to receive a sample of a volume of blood flowing through the cannula, and an uncoupled position in which the reservoir is separated from the exit opening of the cannula and the collection component is held on the housing by means of the fixing element.

One significant advantage which is achieved by the invention over the prior art consists in that, by means of the collection component which is provided, a blood sample is taken from the patient during placement of the indwelling catheter and is stored in the self-filling reservoir, wherein the blood collected here is not yet mixed with substances to be administered later during treatment of the patient. The blood sample stored in this way in the reservoir of the collection component is held on the housing of the placed indwelling catheter by means of the fixing element, and thus is held on the patient. It can thus be ensured that, for a subsequent blood test, in particular to ascertain the patient's blood group, a pretransfusion blood sample is available which was taken before any administration of infusion solution or of emergency blood supplies.

Since the collection component with the reservoir in which the blood sample is stored is attached to the placed indwelling catheter, no loss of the blood sample is possible. The allocation of the subsequently tested blood sample to the patient is also ensured in this way. Only when the blood test is to be carried out is the collection component detached from the placed indwelling catheter. Until this point in time, no loss of the blood sample is possible since the collection component is fixed to the housing of the indwelling catheter.

The described advantages show their effect in particular in connection with the use of the indwelling catheter in the event of an emergency or disaster, in which initially the rapid emergency treatment of the patient takes priority and a blood test is not carried out until later in the hospital.

One purposeful embodiment of the invention may provide that the fixing element has a predetermined breaking point, which makes it easier for the collection component with the blood sample stored in the reservoir to be detached from the housing of the indwelling catheter. The collection component can be separated from the housing without any further aids, for example a pair of scissors.

In order to meet high hygiene and medical requirements, one embodiment of the invention provides that the fixing element is made of a plastic material. By way of example, it may be a plastic strip. This further has the advantage that the fixing element is made of the same material from which usually the housing and most other parts of the indwelling catheter are made.

One purposeful further development of the invention provides that a holding component for holding the collection component is formed on the housing, in order to store the collection component on the housing in a manner uncoupled from the exit opening of the cannula. This prevents the collection component from hanging loose on the housing after placement of the indwelling catheter and removal of the cannula. By means of the holding component, the collection component is fixed in place.

In one preferred embodiment of the invention, the easy arrangement of the collection component in the holding component/removal of the collection component from the holding component is achieved in that the holding component has an insertion opening for the collection component, for example a Luer connection. A plug-in connection is thus formed between the holding component and the collection component by at least partially inserting the collection component into the holding component.

One further development of the invention purposefully provides that the holding component is formed on a support arranged on the housing. As a result, the holding component is arranged in a region which serves to support the indwelling catheter on the skin of the patient, so that, when the collection component is provided, no change in the rest of the design of the housing of the indwelling catheter is necessary.

In one advantageous embodiment of the invention, a partial loss of the collected blood sample and/or possible contamination of the blood sample is prevented in that the holding component is formed as a blind stopper for the collection component. This prevents the penetration of contaminants into the reservoir containing the blood sample.

One preferred embodiment of the invention may provide that a marking area is formed on the collection component. Information about the patient can be written in the region of the marking area, for example using a waterproof pen, so that no mixing-up of the blood samples takes place during the subsequent blood test. In the treatment center, the center's own patient information (sticky label) can be applied to the marking area.

In one purposeful embodiment of the invention, it is provided that the collection component is formed as a closure piece for closing a hollow chamber which is connected to the exit opening of the cannula, wherein the hollow chamber is connected to the reservoir when the collection component is in the coupled position. As a result, the collection component performs not just the function of storing the blood sample but also the function of a closure/end piece during placement of the indwelling catheter.

In one embodiment of the invention, a collection component with expanded functionalities is formed in that an air-permeable filter is arranged in the region of an outflow opening of the closure piece, through which filtered air can escape out of the cannula and into the hollow chamber during the inflow of the volume of blood.

Purposefully, one further development of the invention may provide that the collection component in the coupled position is coupled to a grip piece in which the cannula is held and by means of which the cannula can be guided as it is introduced into/removed from the housing.

In one preferred further development, the removal of the blood sample stored in the reservoir of the collection component for the purpose of carrying out the test is made easier in that the collection component has a closable removal opening connected to the reservoir in order to remove the blood sample.

One further development of the invention may purposefully consist in that a quantity of EDTA crystals is arranged in the reservoir as an anticoagulant, in order to have anticoagulated blood available for determining the blood group.

BRIEF DESCRIPTION OF THE DRAWINGS

The invention will be explained in more detail below on the basis of examples of embodiments and with reference to the figures of the drawing, in which:

FIG. 1 shows a schematic diagram of an indwelling catheter before puncturing; and FIG. 2 shows a schematic diagram of the indwelling catheter according to FIG. 1 after puncturing.

DESCRIPTION OF A PREFERRED EMBODIMENT

FIG. 1 shows a schematic diagram of an indwelling catheter comprising a housing 1, into which a cannula 2 is introduced with the aid of a grip piece 3. The grip piece 3 serves for handling of the cannula 2 as it is introduced into the housing 1 and as it is removed from the housing 1. Formed on the housing 1 are side wings 4 which serve to support the indwelling catheter during placement of the indwelling catheter and thereafter on the skin of the patient. The housing 1 of the indwelling catheter, including the side wings 4, is usually produced as a component made of a plastic material.

A collection component 5, which in the drawings is shown as a connection piece, is inserted into the grip piece 3 from the rear so that a reservoir 7 formed in the collection component 5 is connected to an exit opening at the rear end of the cannula 2, as a result of which part of a volume of blood flowing through the cannula 2 can pass into the reservoir 7 and is stored there as a blood sample. The blood sample stored in the reservoir 7 is collected immediately during placement of the indwelling catheter, so that it is a pretransfusion blood sample. The reservoir 7 automatically fills during placement of the indwelling catheter.

Formed on the collection component 5 is a marking area 6 which is used for writing patient information and/or the name of the person providing treatment (doctor, paramedic) or for affixing a label containing information to identify the patient. Also provided in the region of the marking area 6 is a lid 8 which can be opened in order to remove the blood sample stored in the reservoir 7 for the blood test in the laboratory.

The collection component 5 is connected to the right-hand side wing 4 via a flexible fixing element 9. The flexible fixing element 9 is for example a plastic tab or a plastic strip. The flexible fixing element 9 ensures that the collection component 5 continues to be held on the housing 1 of the indwelling catheter after removal from the grip piece 3 and thus cannot be lost. As shown in FIG. 2, formed on one of the side wings 4 is a holding component 10, in which the collection component 5 is inserted in order to ensure that the latter is fixed in place on the housing 1. Here, the holding component 10 is preferably designed as a blind stopper 12 in order to prevent any blood from running out of the collection component 5.

The flexible connection 9 has a predetermined breaking point 11, so that the collection component 5 can be separated from the housing 1 when the blood test is to be prepared. This takes place for example after the patient has been admitted to a hospital.

The size of the reservoir 7 need only be sufficient to hold a few milliliters of blood, since even such a quantity is sufficient to determine the blood group. The reservoir 7 also contains a defined quantity of EDTA crystals as an anticoagulant for the blood sample.

The features of the invention which are disclosed in the above description, the claims and the drawing may be important both individually and in any combination for implementing the invention in its various embodiments.

The invention claimed is:

1. A system, comprising:
 a housing having an interior;
 a puncturing cannula for being introduced into a body of a patient and configured to be introduced into and/or removed from the housing interior in a longitudinal direction of the housing, the cannula extending through a front housing opening in such a way that an entry opening of the cannula is arranged outside the housing at least in a fully introduced position of the cannula;
 a collection component for storing a blood sample, a flexible fixing element holding the collection component in a movable manner on the housing, the collection component being configured to be displaced between a coupled position, in which a self-filling reservoir formed in the collection component is connected to an exit opening of the cannula in order to receive a sample of a volume of blood flowing through the cannula, and an uncoupled position, in which the reservoir is separated from the cannula and the collection component is held on the housing by means of the fixing element; and
 the housing being configured to be supported on skin of the patient when the cannula is introduced into the body of the patient and when the collection component is in the uncoupled position.

2. The system according to claim 1, wherein the fixing element has a predetermined breaking point.

3. The system according to claim 2, wherein the fixing element is made of a plastic material.

4. The system according to claim 1, wherein the fixing element is made of a plastic material.

5. The system according to claim 1, further comprising a holding component for holding the collection component formed on the housing, in order to store the collection component on the housing when the collection component is uncoupled from the cannula.

6. The system according to claim 5, wherein the holding component has an insertion opening for the collection component.

7. The system according to claim 6, wherein the holding component is formed on a support arranged on the housing.

8. The system according to claim 5, wherein the holding component is formed on a support arranged on the housing.

9. The system according to claim 8, wherein the support arranged on the housing comprises side wings which extend in a direction lateral to a central longitudinal axis of the cannula when the collection component is in the coupled position.

10. The system according to claim 5, wherein the holding component is formed as a blind stopper for the collection component.

11. The system according to claim 1, wherein a marking area is formed on the collection component.

12. The system according to claim 1, a tubular portion of the collection component is formed as a connection piece for connecting the exit opening of the cannula to the reservoir when the collection component is in the coupled position.

13. The system according to claim 12, wherein the connection piece has a common central longitudinal axis with the cannula when the collection component is in the coupled position.

14. The system according to claim 1, further comprising:
 a grip piece to which the collection component in the coupled position is coupled and in which the cannula is held and by means of which the cannula can be guided as the cannula is introduced into and/or removed from the housing.

15. The system according to claim 14, wherein the grip piece has a rear, and the collection component is attached to the rear of the grip piece when the collection component is in the coupled position.

16. The system according to claim 1, wherein the collection component has a closable removal opening connected to the reservoir in order to remove the blood sample.

17. The system according to claim 1, wherein a quantity of EDTA crystals is arranged in the reservoir as an anticoagulant.

18. The system according to claim 1, wherein the housing comprises an indwelling catheter.

19. The system according to claim 1, wherein the housing comprises an indwelling catheter such that the fixing element prevents the collection component from being separated from the patient with the indwelling catheter, and such that the collection component can be removed without removing the housing and the indwelling catheter from the patient.

\* \* \* \* \*